(12) United States Patent
Rubrecht (10) Patent No.: US 11,660,081 B2
(45) Date of Patent: May 30, 2023

(54) SURGICAL INSTRUMENT RETAINER DEVICE

(71) Applicant: MedTech S.A., Montpellier (FR)

(72) Inventor: Rodolphe Rubrecht, Liouc (FR)

(73) Assignee: MedTech S.A., Montpellier (FR)

( * ) Notice: Subject to any disclaimer, the term of this patent is extended or adjusted under 35 U.S.C. 154(b) by 369 days.

(21) Appl. No.: 17/100,100

(22) Filed: Nov. 20, 2020

(65) Prior Publication Data
US 2021/0153852 A1    May 27, 2021

Related U.S. Application Data

(60) Provisional application No. 62/941,341, filed on Nov. 27, 2019.

(51) Int. Cl.
*A61B 17/00* (2006.01)
*A61B 90/50* (2016.01)

(52) U.S. Cl.
CPC .............. *A61B 17/00* (2013.01); *A61B 90/50* (2016.02); *A61B 2017/00477* (2013.01)

(58) Field of Classification Search
CPC ................... A61B 17/00; A61B 90/50; A61B 2017/00477; A61B 17/3403; A61B 2017/3405; A61B 90/11; A61B 2090/0813; A61B 2017/0046
See application file for complete search history.

(56) References Cited

U.S. PATENT DOCUMENTS

| 10,172,641 B2* | 1/2019 | Wachli .................. A61B 17/42 |
| 2013/0317520 A1 | 11/2013 | Choi et al. |
| 2016/0089181 A1 | 3/2016 | Johnson |
| 2018/0168743 A1 | 6/2018 | Schmid et al. |
| 2019/0192254 A1 | 6/2019 | Garbus et al. |
| 2020/0289227 A1 | 9/2020 | Jiang et al. |
| 2021/0153914 A1* | 5/2021 | Lomeli ............. A61B 17/7074 |

FOREIGN PATENT DOCUMENTS

WO    WO-2019056871 A1    3/2019

OTHER PUBLICATIONS

"European Application Serial No. 20210137.4, Decision to Grant a European Patent dated Jun. 30, 2022", 2 pgs.
"European Application Serial No. 20210137.4, Extended European Search Report dated Apr. 12, 2021", 6 pgs.
"European Application Serial No. 20210137.4, Response filed Dec. 2, 2021 to Extended European Search Report dated Apr. 12, 2021", 48 pgs.

* cited by examiner

*Primary Examiner* — Jonathan T Kuo
*Assistant Examiner* — Charlie D Norman-Blakeney
(74) *Attorney, Agent, or Firm* — Schwegman Lundberg & Woessner, P.A.

(57) ABSTRACT

A surgical instrument retainer can include a proximal component and a distal component. The proximal component can include a head, a first body, and a proximal plurality of projections. The distal component can define a second instrument bore and a body bore and can include a distal plurality of projections. The can head engageable with the end effector coupler to position the instrument retainer within the end effector coupler.

20 Claims, 9 Drawing Sheets

SURGICAL INSTRUMENT RETAINER DEVICE

CLAIM OF PRIORITY

This application claims the benefit of priority to U.S. Provisional Application Ser. No. 62/941,341, filed on Nov. 27, 2019, which is incorporated herein by reference in its entirety.

BACKGROUND

During robotic surgeries, surgical instruments such as needles, guide wires, guide tubes, and others can be inserted into a patient's anatomy by passing through a surgical guide. The surgical instruments can be accurately maintained on a planned trajectory within the surgical guide by a robotic arm to reach a planned target point. Because it may be difficult or undesirable to manually hold a surgical instrument for an extended length of time, mechanical and/or electromechanical arms can be used to accurately maintain a specific position and orientation of a surgical instrument while aspects of a surgical procedure are performed. Some robotic arms can be adjustable, such that a position of the arm can be adjusted before or during the surgical procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description and the drawings sufficiently illustrate specific examples to enable those skilled in the art to practice them. Other examples may incorporate structural, process, or other changes. Portions and features of some examples may be included in, or substituted for, those of other examples. Examples set forth in the claims encompass all available equivalents of those claims.

Various surgical guides exist for holding and guiding surgical instruments during a surgical procedure. When a surgical instrument passes through a surgical guide, such as a guide tube, friction is generated between the surface of the surgical instrument and the walls of the guide tube. Often, guide tubes are comprised of a single component and include a longitudinal bore for a surgical instrument to pass through. As the surgical instrument contacts the entire length of the longitudinal bore, a significant amount of friction can be generated. The amount of friction between the guide tube and the surgical instrument typically increases over time, as cleaning and sterilization cycles damage the surfaces of the surgical instrument and the guide tube. Friction values can also increase during a surgical procedure if fluids or solid particles from a patient stick to the surgical instrument or the guide tube. Friction can generate a significant amount of heat, which increases the risk of surgical instrument breakage, deformation, or tissue damage due to a high instrument temperature.

Additionally, friction between the guide tube and the surgical instrument can prevent the instrument from sliding within the guide tube, which can force a surgeon to withdraw and replace the guide tube or the surgical instrument during a surgical procedure. Withdrawing and replacing surgical equipment during a procedure can increase the risk of infection for a patient and lengthen the procedure.

This disclosure can address these issues, among others, by providing a surgical instrument retainer that can help to consistently decrease friction during use of the retainer, including over the life of the retainer, while maintaining a precise fit between the surgical instrument and the retainer by providing a retainer that includes projections configured to engage a surgical instrument, to provide reduced surface contact between the surgical instrument and the surgical instrument retainer. The surgical instrument retainer of the present disclosure is also capable of being comprised of two pieces in order to improve the ease and quality of cleaning and sterilization.

Figure 1A:
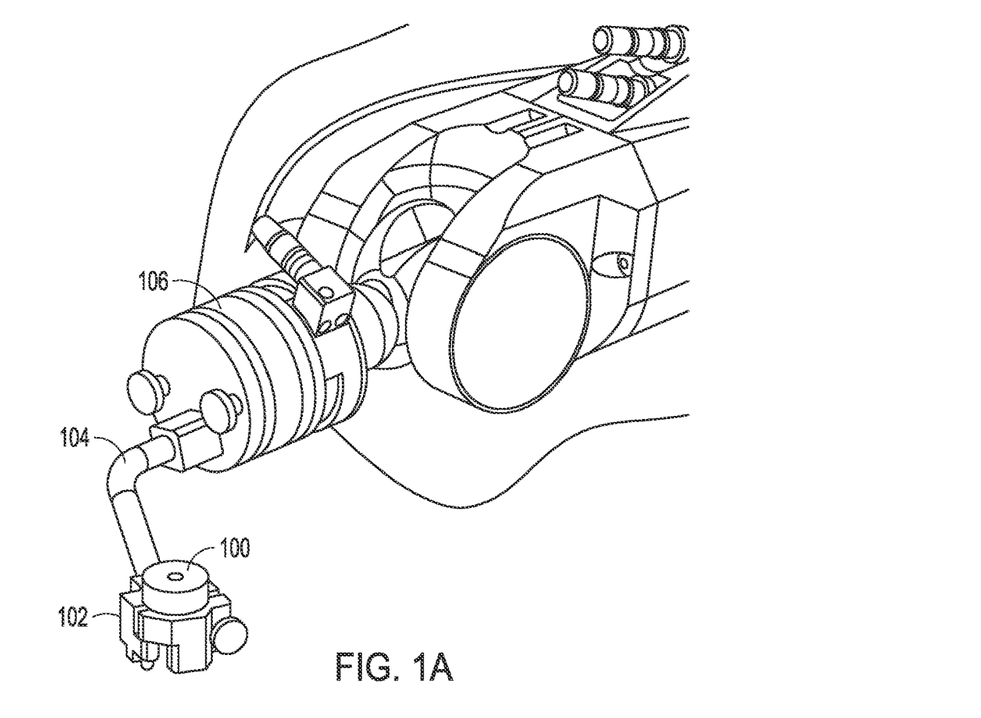
FIG. 1A illustrates an isometric view of a surgical instrument retainer in an end effector coupler of a surgical arm, in accordance with at least one example of the present application.
Figure 1B:
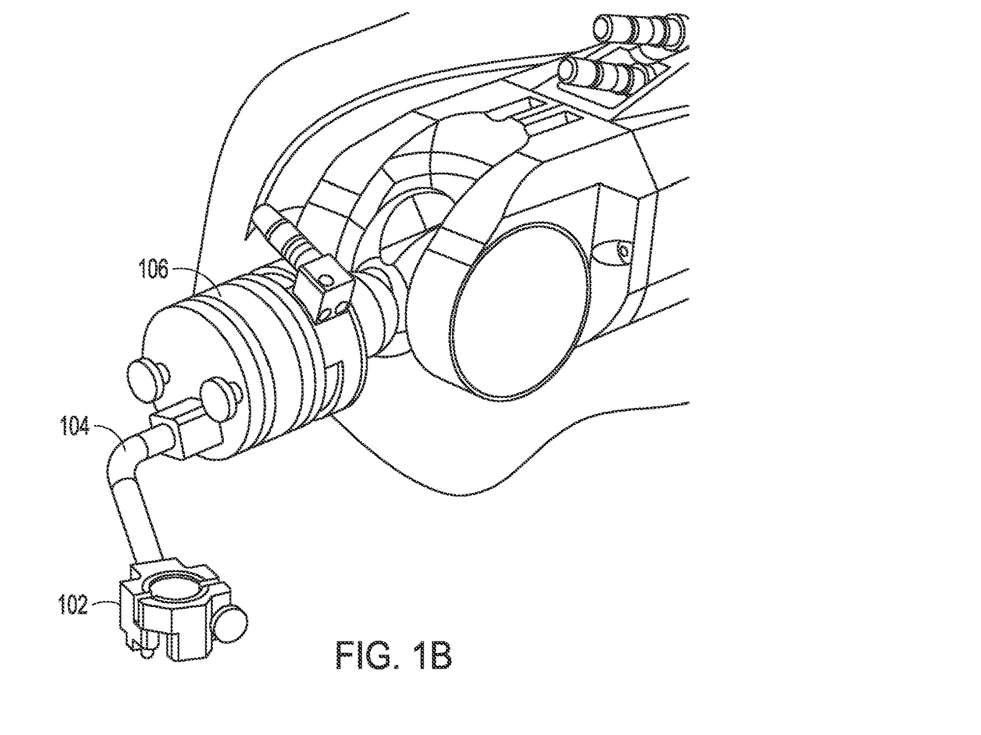
FIG. 1B illustrates an isometric view of an end effector coupler of a surgical arm, in accordance with at least one example of the present application.

FIG. 1A illustrates an isometric view of a surgical instrument retainer in an end effector coupler of a surgical arm, in accordance with at least one example of the present application. FIG. 1B illustrates an isometric view of an end effector coupler of a surgical arm, in accordance with at least one example of the present application. FIGS. 1A and 1B are discussed below concurrently.

As shown in FIG. 1A, a surgical instrument retainer 100 can be configured to be receivable within an end effector coupler 102. The end effector coupler 102 can be coupled to an end effector 104 of a surgical arm 106. The surgical instrument retainer 100 can be configured to engage with various styles of pre-existing end effector couplers 102 that can be used with the end effector 104 of the surgical arm 106.

During a surgical procedure, surgical instruments can reach a planned target point within a patient's anatomy by passing through the surgical instrument retainer 100. In some procedures, the surgical instrument retainer 100 can accurately retain a surgical instrument in a specific position for an extended length of time. The surgical arm 106 can adjust the position surgical instrument retainer 100 before or during the surgical procedure. In operation of some examples, the surgical arm 106 can be used to position the end effector 104 and the end effector coupler 102 in a planned position. The surgical instrument retainer 100 can be inserted into the end effector coupler 102.

Once positioned within the end effector coupler 102, the surgical instrument retainer 100 can receive a surgical instrument through an instrument bore of the surgical retainer 100 and can retain a surgical instrument therein. The surgical instrument retainer 100 can guide translation of a surgical instrument within the surgical instrument retainer 100, with respect to the surgical instrument retainer 100, the end effector coupler 102, and the end effector 104, and further with respect to a patient during the surgical procedure. After the surgical procedure, the surgical instrument retainer 100 can be removed from the end effector coupler 102. The surgical instrument retainer 100 can then be cleaned and sterilized in an autoclave in preparation for a future surgical procedure. The surgical instrument retainer 100 can thereby help perform one or more operations of a surgical procedure.

Figure 2A:
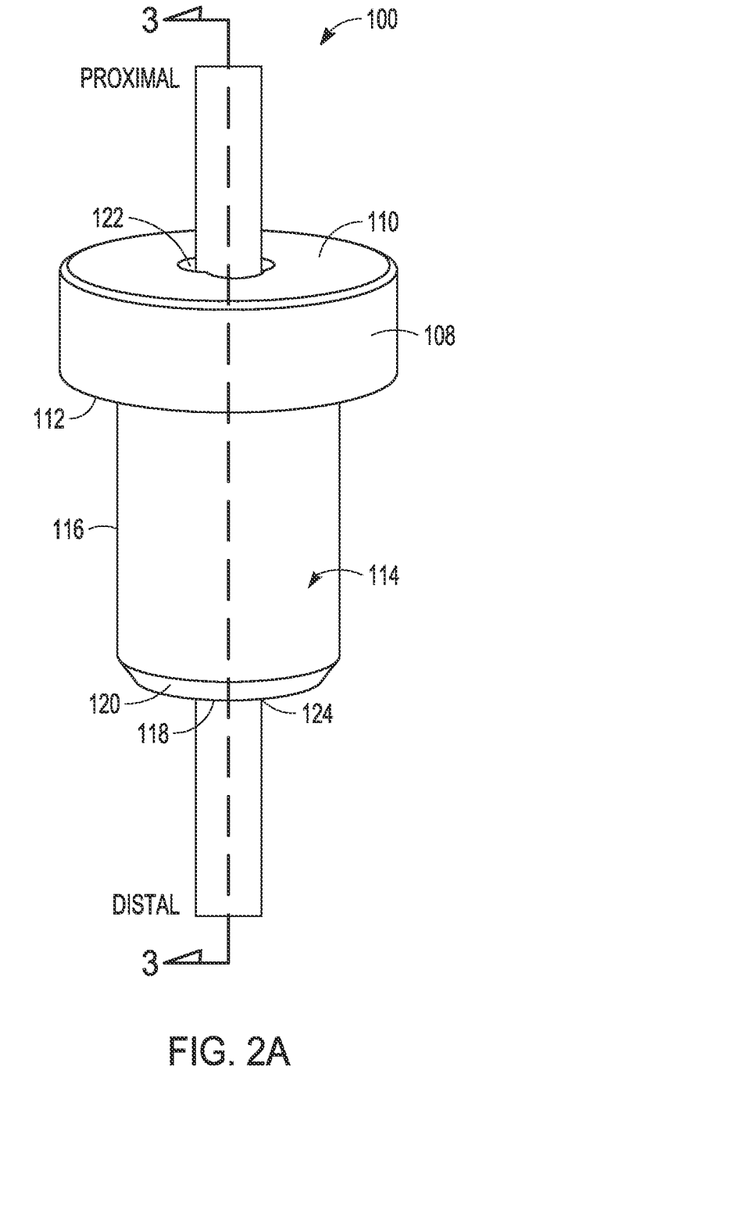
FIG. 2A illustrates an isometric view of a surgical instrument retainer, in accordance with at least one example of the present application.
Figure 2B:
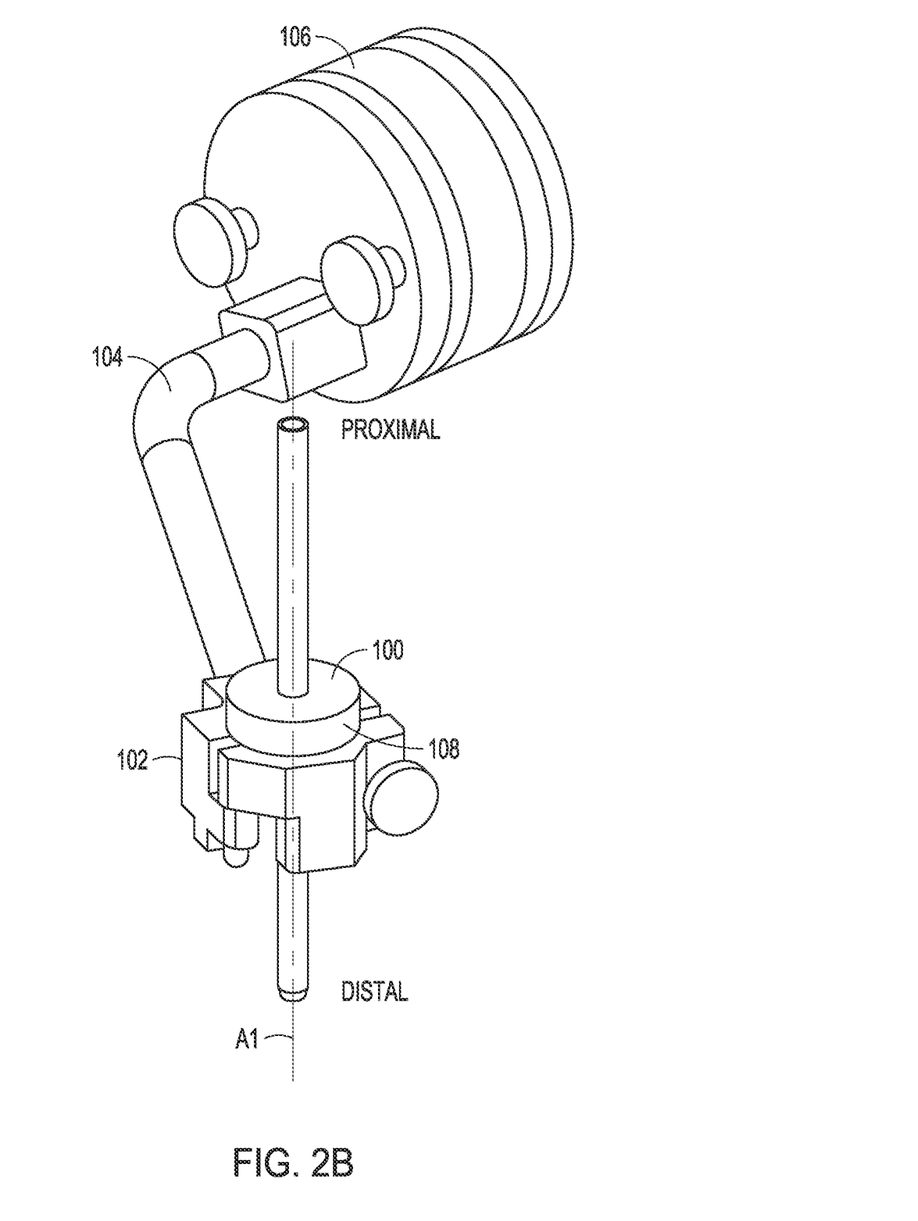
FIG. 2B illustrates an isometric view of a surgical instrument retainer in an end effector coupler of a surgical arm, in accordance with at least one example of the present application.

FIG. 2A illustrates an isometric view of a surgical instrument retainer 100, in accordance with at least one example of the present application. FIG. 2B illustrates an isometric view of a surgical instrument retainer 100 in an end effector coupler of a surgical arm, in accordance with at least one example of the present application. Also shown in FIGS. 2A-2B are longitudinal axis A1, section indicators 3-3, and orientation indicators Proximal and Distal. FIGS. 2A and 2B are discussed below concurrently. The surgical instrument retainer 100 can include a head 108, a head proximal surface 110, a head distal surface 112, a distal component 114, an outer surface 116, a distal component end 118, a distal component chamfer 120, a first instrument bore 122, and a second instrument bore 124.

The surgical instrument retainer 100 can include the head 108. The head 108 can be generally cylindrical in shape. The head 108 can alternatively form a cuboid, a triangular prism, a rectangular prism, a hexagonal prism, an octagonal prism, or the like. The head can include the head proximal surface 110 and the head distal surface 112. The head proximal surface 110 and the head distal surface 112 can extend laterally beyond a width of the distal component 114.

The distal component 114 can extend substantially along the longitudinal axis A1. The distal component 114 can be generally cylindrical in shape. The distal component 114 can alternatively from a cuboid, a triangular prism, a rectangular prism, a hexagonal prism, an octagonal prism, or the like. The distal component 114 can be coupled to the head 108. The distal component 114 can include the distal component chamfer 120. The distal component chamfer 120 can be formed in the outer surface 116 of the distal component 114. The distal component chamfer 120 can aid in inserting the surgical instrument retainer 100 into the end effector coupler 102 by forming a taper in the distal component end 118.

The head 108 can include the first instrument bore 122. The first instrument bore 122 can extend through the head proximal surface 110 and the head distal surface 112, along the longitudinal axis A1. The distal component 114 can include the second instrument bore 124. The second instrument bore 124 can extend through the distal component end 118 of the distal component 114, along the longitudinal axis A1. The first instrument bore 122 and the second instrument bore 124 can be configured to have a substantially identical dimensions in some examples; and can be configured to have different bore diameters and/or shapes in other examples. The first instrument bore 122 and the second instrument bore 124 can together extend entirely through a longitudinal length of the surgical instrument retainer 100, when the head 108 is connected to the distal component 114.

The first instrument bore 122 and the second instrument bore 124 can be configured to accept a surgical instrument 126. The surgical instrument 126 can be, for example, a cylindrical guide tube as shown in FIG. 2A. The surgical instrument 126 can be other types of surgical instruments and can comprise other shapes, such as a cuboid, a triangular prism, a rectangular prism, a hexagonal prism, an octagonal prism, or the like. The surgical instrument 126 can extend through the first instrument bore 122 and the second instrument bore 124, to extend entirely through surgical instrument retainer 100. The surgical instrument retainer 100 can be configured to allow the surgical instrument 126 to translate proximally and distally along the longitudinal axis A1; within the surgical instrument retainer 100.

In some examples, the surgical instrument retainer 100 can be inserted into the end effector coupler 102 of the surgical arm 106, which can be positioned in preparation for a surgical procedure. When positioned within the end effector coupler 102, the head distal surface 112 can contact the end effector coupler 102 to limit distal translation of the surgical instrument retainer 100 within the end effector coupler 102. The outer surface 116 of the distal component 114 can also contact the end effector coupler 102 to help position the surgical instrument retainer 100 within the end effector coupler 102, and also to help limit lateral movement of the surgical instrument retainer 100 with respect to the end effector coupler 102.

The surgical instrument 126 can be inserted into the surgical instrument retainer 100 by passing through the first instrument bore 122 and through the second instrument bore 124, along the longitudinal axis A1. Securing of the surgical instrument 126 to the instrument retainer 100 can be performed either before or after securing the instrument retainer 100 within the end effector coupler 102. The surgical instrument retainer 100 can position and hold the surgical instrument 126 during a surgical operation 100. The surgical instrument retainer 100 can also precisely guide proximal and distal translation of the surgical instrument 126 during a surgical procedure.

Figure 3A:
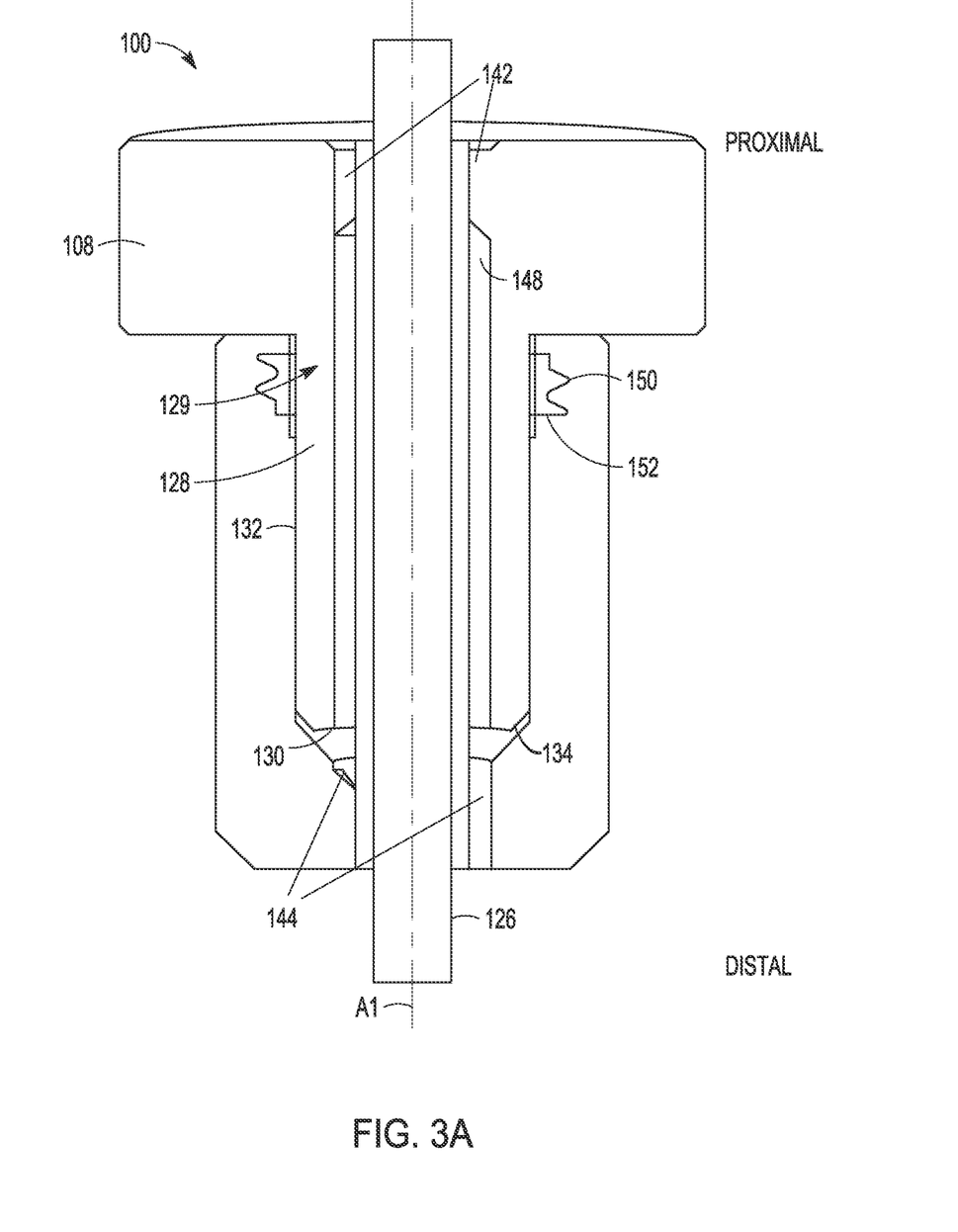
FIG. 3A illustrates a cross-section across indicators 3-3 of FIG. 2A of the instrument retainer engaging a surgical instrument, in accordance with at least one example of the present application.
Figure 3B:
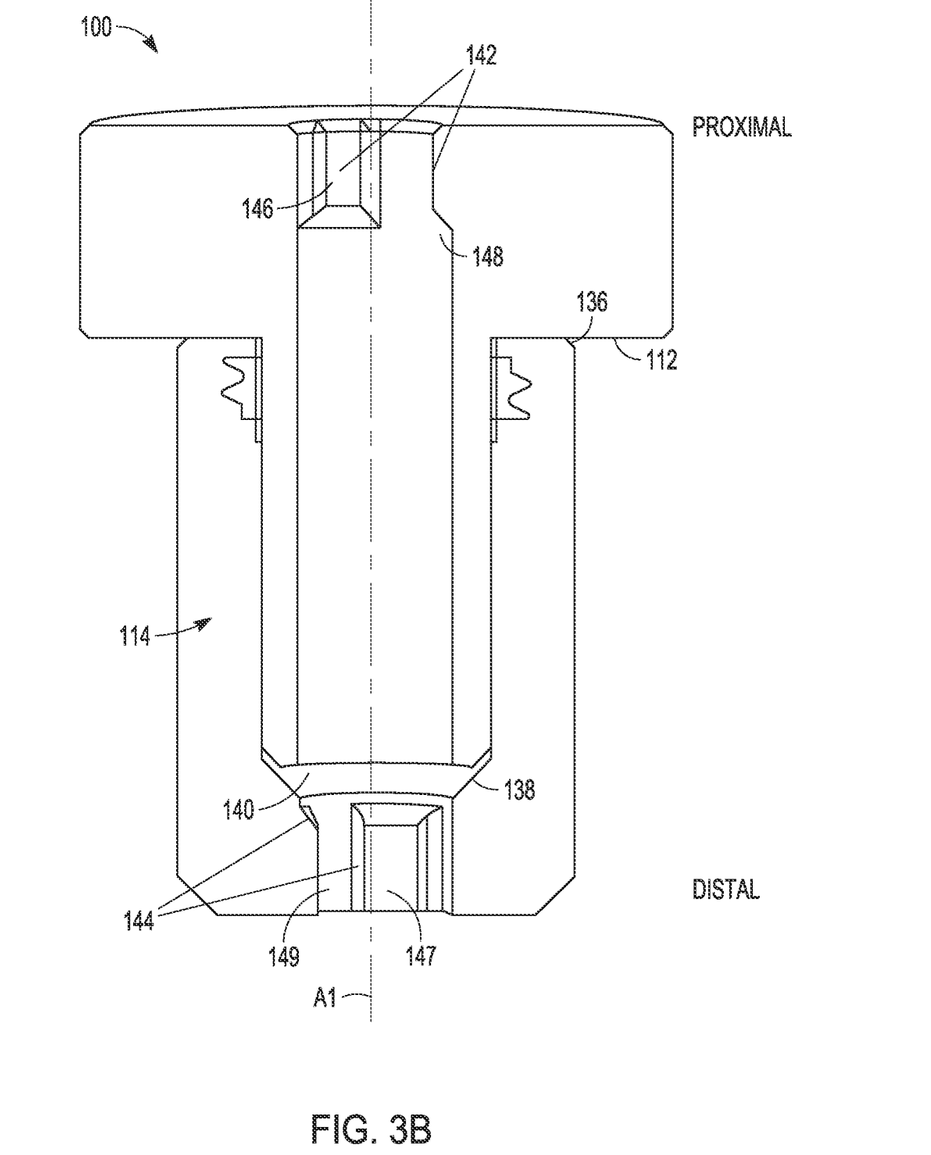
FIG. 3B illustrates a cross-section across indicators 3-3 of FIG. 2A of the surgical instrument retainer, in accordance with at least one example of the present application.

FIG. 3A illustrates a cross-section across section indicators 3-3 of the instrument retainer 100 engaging a surgical instrument, in accordance with at least one example of the present application. FIG. 3B illustrates a cross-section across section indicators 3-3 of the surgical instrument retainer 100, in accordance with at least one example of the present application. FIGS. 3A and 3B also show longitudinal axis A1 and orientation indicators Proximal and Distal. FIGS. 3A and 3B are discussed below concurrently.

The surgical instrument retainer 100 can include a proximal component 129 and the distal component 114. The proximal component 129 can include the head 108 and a first body 128. The first body 128 can include a first body distal surface 130, a first body outer surface 132, and a chamfer edge 134. The distal component 114 can include a distal component proximal surface 136, a body bore 138, and a chamfer 140. The surgical instrument retainer 100 can also include a proximal plurality of projections 142, a distal plurality of projections 144, proximal contacting surfaces 146, distal contacting surfaces 147, a radial extension 148, gaps 149, a first series of coupling threads 150, and a second series of coupling threads 152.

The surgical instrument 100 can include the proximal component 129 and the distal component 114. The first body 128 can extend distally from the head 108, and can be generally cylindrical in shape, but can have other shapes in other examples. The first body 128 and the head 108 can together form the proximal component 129. The first body 128 can include the first body distal surface 130, which can be a distal end or end surface of the first body 128. The first body 128 can also include the first body outer surface 132. The first body outer surface 132 can be a radial or lateral outer surface of the first body 128, extending between the head distal surface 112 and the first body distal surface 130. The first body 128 can include the chamfer edge 134. The chamfer edge 134 can be formed in one or both of the first body distal surface 130 and the first body outer surface 132. The chamfer edge 134 can be a chamfer or bevel connecting the first body outer surface 132 and the first body distal surface 130 to form a distal taper in the first body 128.

The distal component 114 can include the body bore 138. The body bore 138 can be a bore extending through the distal component proximal surface 136. The body bore 138 can extending within the distal component 114 along the longitudinal axis A1. The body bore 138 can include the chamfer 140. The chamfer 140 can be formed within the body bore 138 of the distal component 114, to form a tapered transition between the body bore 138 and the second instrument bore 124. The chamfer 140 can be formed proximally to the distal component end 118 within the body bore 138. The chamfer 140 can be formed distally to the first body 128, when the first body 128 and the distal component 114 are coupled, such that the chamfer 140 can aid in inserting the first body 128 into the body bore 138 of the distal component 114. In some examples, the chamfer 140 can be configured to correspondingly engage the chamfer edge 134 of the first body 128, to position the first body 128 within the body bore 138 of the distal component 114.

The surgical instrument retainer 100 can include the proximal plurality of projections 142 and the distal plurality of projections 144. The proximal plurality of projections 142 can extend radially (or laterally) from the first instrument bore 122 of the proximal component and can terminate therein. In some examples, the proximal plurality of projections 142 can be positioned near a proximal opening of the first instrument bore 122. Similarly, the distal plurality of projections 144 can extend radially (or laterally) into the second instrument bore 124 of the distal component 114. In some examples, the distal plurality of projections 144 can be positioned near a distal opening of the second instrument bore 124. The proximal plurality of projections 142 and the distal plurality of projections 144 can be positioned in various orientations within the first instrument bore 122 and the second instrument bore 124, respectively.

The proximal plurality of projections 142 can include the proximal contacting surfaces 146. The distal plurality of projections 144 can include the distal contacting surfaces 147. In some examples, the proximal plurality of projections 142 and the distal plurality of projections 144 can be configured to have a substantially identical dimensions. The proximal contacting surfaces 146 and the distal contacting surfaces 147 can be configured to be correspondingly shaped to the surgical instrument 126. For example, the proximal contacting surfaces 146 and the distal contacting surfaces 147 can form concave shapes configured to correspond to a convex exterior surface of the cylindrically shaped surgical tool 126, as shown in FIGS. 3A-3B.

The proximal plurality of projections 142 and the distal plurality of projections 144 can define a radial extension 148. The radial extension 148 can be a distance one or more of the proximal plurality of projections 142 and the distal plurality of projections 144 extend inward into the first instrument bore 122 and the second instrument bore 124, respectively. The proximal plurality of projections 142 and the distal plurality of projections 144 can be configured to have a substantially identical radial extension 148 to precisely retain a surgical instrument. The radial extension 148 can be, for example, 1-2 millimeters, 3-4 millimeters, 5-6 millimeters, 7-8 millimeters, or 1-10 millimeters. The radial extension 148 can be sufficient to ensure that the surgical instrument 126 contacts only the proximal contacting surfaces 146 and the distal contacting surfaces 147, of the proximal plurality of projections 142 and the distal plurality of projections 144, respectively.

The surgical instrument retainer 100 can include the gaps 149, which can be defined as a circumferential or angular space between each of the proximal plurality of projections 142 and the distal plurality of projections 144. The proximal component 129 can be coupled to the distal component 114. The proximal component can include the first series of coupling threads 150. The distal component 114 can include the second series of coupling threads 152. The second series of coupling threads 152 can be configured to engage the first series of coupling threads 150 to couple the proximal component 129 to the distal component 114, as shown in FIGS. 3A-3B. Alternatively, the proximal component 129 and the distal component 114 can be welded together, or otherwise coupled in a non-separable manner.

When the surgical instrument retainer 100 is assembled, the first body 128 can be inserted into the body bore 138 of the distal component 114. The distal component outer surface 132 can contact the body bore 138 to position the first body 128 within the distal component 114. The proximal component 129 can then be rotated within the body bore 138, to engage the first series of coupling threads 150 on the proximal component 129 with the second series of coupling threads on the distal component 114, to couple the proximal component 129 to the distal portion 114. When the proximal component 129 is coupled to the distal component 114, the first instrument bore 122 and the second instrument bore 124 can become coaxial with the axis A1. Such alignment can also align the proximal plurality of projections 142 and the distal plurality of projections 144, such that the proximal contacting surfaces 146 and the distal contacting surfaces 147 are substantially equidistant from the axis A1.

In operation, the proximal contacting surfaces 146 of the proximal plurality of projections 142 and the distal contacting surfaces 147 of the distal plurality of projections 144 can engage the surgical instrument 126 to position the instrument 126 relative to the proximal component 129 and the distal component 114. The proximal plurality of projections 142 and the distal plurality of projections 144 can be configured such that the proximal contacting surfaces 146 and the distal contacting surfaces 148 precisely conform to the dimensions of the surgical instrument 126. A precise fit between the surgical instrument 126 and the proximal 146 and distal 147 contacting surfaces can ensure the surgical instrument retainer 100 can provide accurate retention of the surgical instrument 126, in order to reach a planned target point of a surgical procedure.

Because the total surface area of all of the proximal contacting surfaces 146 and the distal contacting surfaces 147 can be much less than the total surface area of the first instrument bore 122 and the second instrument bore 124, the amount of friction between the surgical instrument 126 and the proximal 146 and distal 147 contacting surfaces 147 can accordingly be much less that it would otherwise be; if the surgical instrument contacted the first instrument bore 122 and the second instrument bore 124. The proximal plurality of projections 142 and the distal plurality of projections 144 can therefore provide the benefit of reducing friction during proximal and distal translation of the surgical instrument 126 within the surgical instrument retainer 100.

Also, during a surgical procedure, the surgical instrument 126 can become covered in fluids, which can greatly increase friction between the surgical instrument 126 and the surgical instrument retainer 100. In some examples, the gaps 149 between each of the proximal plurality of projections 142 and each of the distal plurality of projections 144 can allow for fluids to more easily pass through the instrument bore 122 and 124, which can further help to reduce friction between the surgical instrument 126 and the retainer 100, especially during translation of the surgical instrument 126 relative to the surgical instrument retainer 100.

Figure 4:
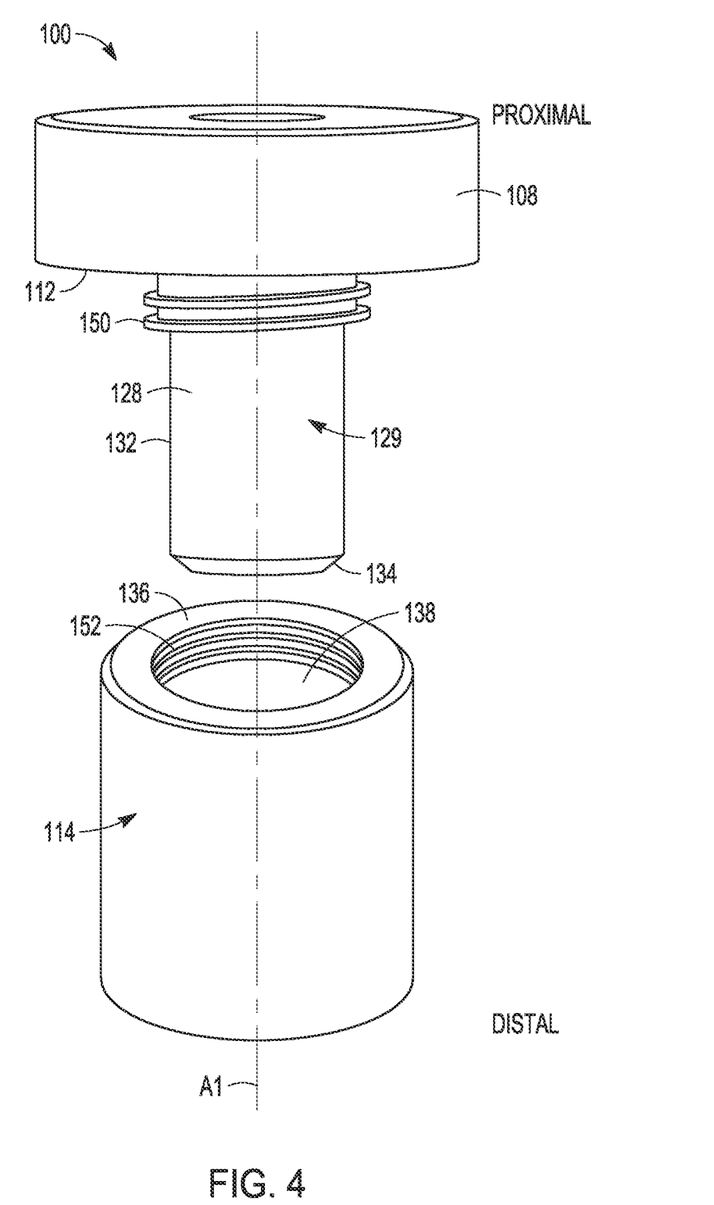
FIG. 4 illustrates an exploded view of a surgical instrument retainer, in accordance with at least one example of the present application.

FIG. 4 illustrates an exploded view of the surgical instrument retainer 100, in accordance with at least one example of the present application. FIG. 4 also shows longitudinal axis A1 and orientation indicators Proximal and Distal. The first body 128 of the proximal component 129 can be configured to be insertable into the distal component 114. The proximal component 129 and the distal component 114 can be formed as two separate pieces configured to be selectively coupled together using the coupling threads 150 and 152.

The first series of coupling threads 150 can be formed on a generally proximal portion of the first body 128 and can extend radially outward from the first body outer surface 132. The second series of coupling threads 152 can be formed in a generally proximal portion of the body bore 138 of the distal component 114. The body bore 138 can be formed in the distal component 114 and can extend along the longitudinal axis A1.

The body bore 138 can be configured to accept the first body 128 therein. When assembled, the first body outer surface 132 can contact the body bore 138 to laterally position and center the first body 128 within the distal component 114. The first body outer surface 132 can also contact the body bore 138 to guide the first series of coupling threads 150 to the second series of coupling threads 152. The head distal surface 112 can contact the distal component proximal surface 136, to limit proximal translation of the distal component 114 with the respect to the first body 128.

The ability of the proximal component 129 to be selectively coupled to the distal component 114 can provide the benefit of improving the ease, and quality of, cleaning and sterilization of the surgical instrument retainer 100. For example, in preparation for autoclaving after a surgical procedure, the proximal component 129 can de-coupled from the distal component 114. This can allow for much greater exposure to the interior of the first instrument channel 122, the second instrument 124, and the body bore 138; than would otherwise be possible with a single piece design.

In some examples, the proximal component 129 can be coupled or fastened to the distal component 114 using additional or alternative means, such as fasteners, adhesives, welding, or the like. In some examples, the proximal component and the distal component 114 can be formed together as a single piece, such as through lathe operations, casting, or three-dimensional printing.

Figure 5A:
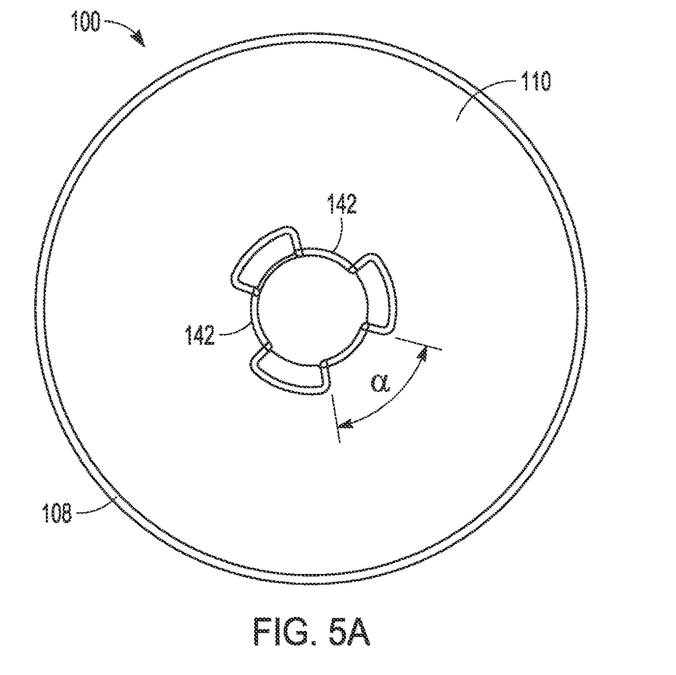
FIG. 5A illustrates a proximal view of the surgical instrument retainer, in accordance with at least one example of the present application.
Figure 5B:
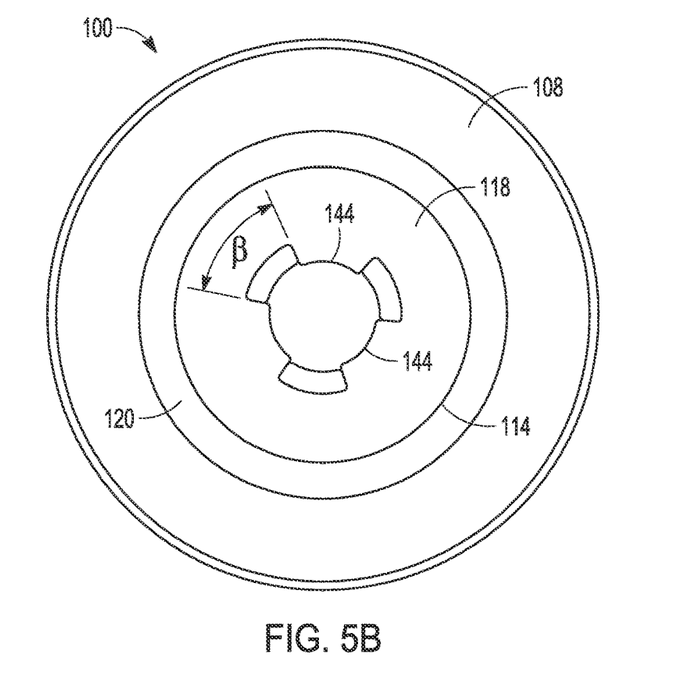
FIG. 5B illustrates a distal view of the surgical instrument retainer, in accordance with at least one example of the present application.

FIG. 5A illustrates a proximal view of the surgical instrument retainer 100, in accordance with at least one example of the present application. FIG. 5B illustrates a distal view of the surgical instrument retainer 100, in accordance with at least one example of the present application. FIGS. 5A and 5B are discussed below concurrently.

The proximal plurality of projections 142 and the distal plurality of projections 144 can extend radially into the first instrument bore 122 and the second instrument bore 124, respectively. The proximal plurality of projections 142 and the distal plurality of projections 144 can be positioned in a variety of different positions and orientations within the first instrument bore 122 and the second instrument bore 124. The proximal plurality of projections 142, including the proximal contacting surfaces 146, and the distal plurality of projections 144, including distal contacting surfaces 147, can be axially aligned; or can be axially staggered as show in FIGS. 5A-5B. For example, if the proximal plurality of projections 142 and the distal plurality of projections 144 are axially staggered, each of the proximal plurality of projections 142 and the proximal contacting surfaces 146 will be each be aligned along a separate longitudinal axis from each of the distal plurality of projections 144 and the distal contacting surfaces 147. Additionally, an axially staggered orientation can help to provide complete circumferential contact with the surgical instrument 126, to precisely center the surgical instrument 126 within the surgical instrument retainer 100. The proximal plurality of projections 142 and the distal plurality of projections 144 can also be positioned in additional proximal or distal orientations within the first instrument bore 122 and the second instrument bore 124; relative to the examples shown in FIGS. 5A-5B.

The proximal plurality of projections 142 and the distal plurality of projections 144 can each include various numbers of projections. In one example, the proximal plurality of projections 142 and the distal plurality of projections 144 can each include three projections. In other examples, the proximal plurality of projections 142 and the distal plurality of projections 144 can also include four, five, or six projections. Each of the proximal contacting surfaces 146 of the proximal plurality of projections 142 and the distal contacting surfaces 147 of the distal plurality of projections 144 can be radially spaced depending on the specific number of projections each of the proximal plurality 142 and the distal plurality of projections 144 includes. Angle α can represent the radial spacing of the proximal plurality of projections 142 and the distal plurality of projections 144.

For example, if the proximal plurality of projections 142 and the distal plurality of projections 144 each include three projections, the angle α between each of the proximal contacting surfaces 146 or distal contacting surfaces 147 can be about 60 degrees. If the proximal plurality 142 and the distal plurality 144 of projections each include four projections, the angle α between each of the proximal contacting surfaces 146 or the distal contacting surfaces 147 can about 45 degrees. If the proximal plurality 142 and the distal plurality 144 of projections each include five projections, the angle α between each of the proximal contacting surfaces 146 or the distal contacting surfaces 147 can about 36 degrees. If the proximal plurality 142 and the distal plurality 144 of projections each include six projections, the angle α between each of the proximal contacting surfaces 146 or the distal contacting surfaces 147 can about 30 degrees.

The surgical instrument retainer can include the gaps 149, which can be defined as a circumferential or angular space between each of the proximal plurality of projections 142 and the distal plurality of projections 144. The gaps 149 can be positioned in a variety of different positions and orientations within the first instrument bore 122 and the second instrument bore 124. The gaps 149 can be axially aligned; or can be axially staggered as show in FIGS. 5A-5B.

The gaps 149 can radially or laterally space the proximal plurality of projections 142 and the distal plurality of projections 144. Angle R can represent the radial space of the gaps 149. The gaps 149 may also form a variety of different spacings depending on the number of projections the proximal plurality 142 and the distal plurality 144 include. For example, if the proximal plurality 142 and the distal plurality 144 of projections each include three projections, the angle θ can be about 60 degrees. If the proximal plurality 142 and the distal plurality 144 of projections each include four projections, the angle $ can be about 45 degrees. If the proximal plurality 142 and the distal plurality 144 of projections each include five projections, the angle β can be about 36 degrees. If the proximal plurality 142 and the distal plurality 144 of projections each include six projections, the angle β can be about 30 degrees.

Figure 6A:
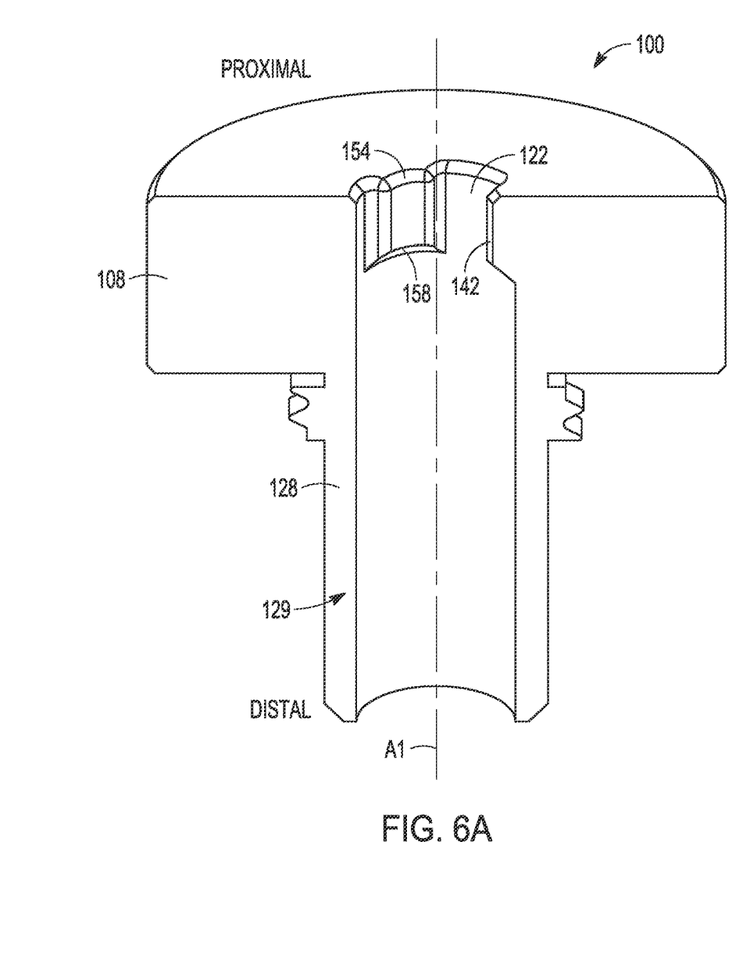
FIG. 6A illustrates a cross-section of a proximal component of the surgical instrument retainer, in accordance with at least one example of the present application.
Figure 6B:
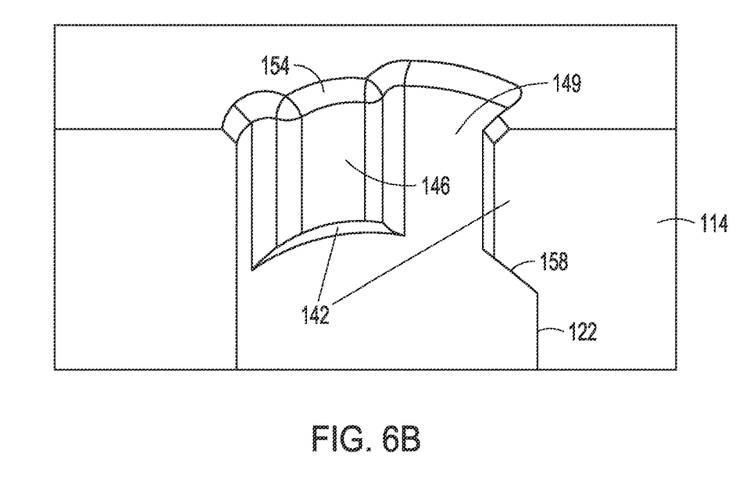
FIG. 6B illustrates a focused cross-section of a portion of the surgical instrument retainer, in accordance with at least one example of the present application.

FIG. 6A illustrates a cross-section of a proximal component of the surgical instrument retainer 100, in accordance with at least one example of the present application. FIG. 6B illustrates a focused cross-section of a portion of the surgical instrument retainer 100, in accordance with at least one example of the present application. FIG. 6A also shows longitudinal axis A1 and orientation indicators Proximal and Distal. FIGS. 6A and 6B are discussed below concurrently.

Each projection of the proximal plurality of projections 142 can include a proximal beveled edge 154. The proximal beveled edges 154 can be formed in the head proximal surface 110 of the proximal component 129. The proximal beveled edges 154 can form a transition between the head proximal surface 110 and the proximal contacting surfaces 146 of the proximal plurality of projections 142. The proximal beveled edges 154 can be chamfers or bevels connecting the head proximal surface 110 and the first instrument bore 122. The proximal beveled edges 154 can form a taper to aid in inserting the surgical tool into the first instrument bore 122; and aid in guiding the surgical tool 126 between the proximal contacting surfaces 146.

Each projection of the proximal plurality of projections 142 can also include a distal beveled edge 158. The distal beveled edge 158 of each of the proximal plurality of projections 142 can be formed in the first instrument bore 122; within the proximal component 129. The distal beveled edges 158 can form a transition between the proximal contacting surfaces 146 of the proximal plurality of projections 142 and the first instrument bore 122. The distal beveled edges 158 can form a taper to aid in guiding the surgical tool 126 between the proximal contacting surfaces 146.

Figure 7A:
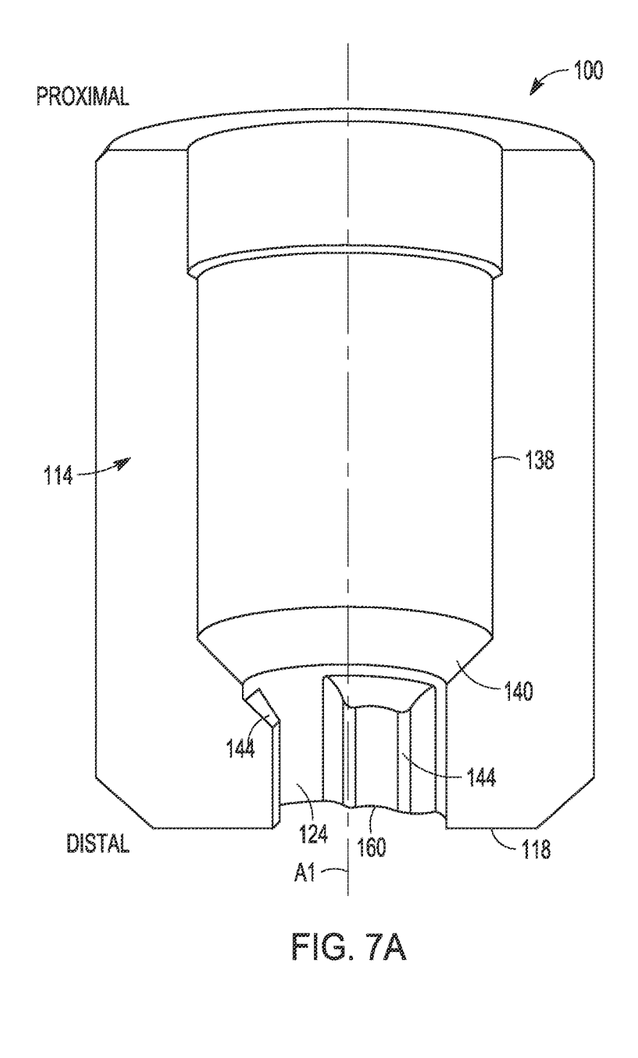
FIG. 7A illustrates a cross-section of a distal component of the surgical instrument retainer, in accordance with at least one example of the present application.
Figure 7B:
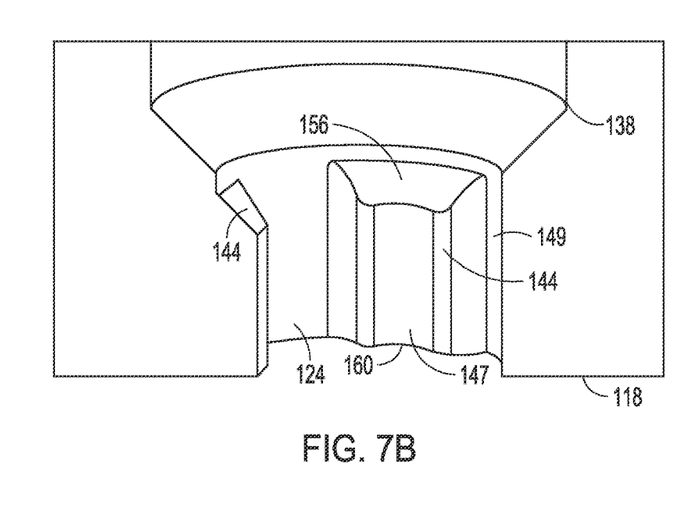
FIG. 7B illustrates a cross-section of a portion of the surgical instrument retainer, in accordance with at least one example of the present application.

FIG. 7A illustrates a cross-section of a distal component of the surgical instrument retainer 100, in accordance with at least one example of the present application. FIG. 7B illustrates a cross-section of a portion of the surgical instrument retainer 100, in accordance with at least one example of the present application. FIG. 7A also shows longitudinal axis A1 and orientation indicators Proximal and Distal. Each projection of the distal plurality of projections 144 can include a proximal beveled edge 156. The proximal beveled edges 156 of each of the distal plurality of projections 144 can be formed in the second instrument bore 124. The proximal beveled edges 156 can form a transition between the second instrument bore 124 and the distal contacting surfaces 147 of the distal plurality of projections 144. The proximal beveled edges 156 can form a taper to aid in guiding the surgical tool 126 from the proximal plurality of projections 142; to between the distal contacting surfaces 147 of the distal plurality of projections 144.

Each projection of the distal plurality of projections 144 can also each include a distal beveled edge 160. The distal beveled edges 160 of each of the distal plurality of projections 144 can be formed in the distal end 118 of the distal component 114. The distal beveled edges 160 can form a transition between the distal contacting surfaces 147 of the distal plurality of projections 144 and the distal component end 118. The distal beveled edges 160 can be chamfers or bevels connecting the distal end 118 and the second instrument bore 124. The distal beveled edges 160 can form a taper to aid in guiding the surgical tool 126 between distal component end 118 and the contacting surfaces 147 of the distal plurality of projections 144.

The surgical instrument retainer 100 of the present disclosure can provide a number of benefits including reducing friction during proximal or distal translation of the surgical instrument 126 within the surgical instrument retainer 100, while retaining precise positioning and retention of the surgical instrument 126. The surgical instrument retainer 100 can also reduce the risk of patient infection by improving the ease and quality of cleaning and sterilization, by utilizing a two-piece design comprised of a proximal component 129 and a distal component 114. The surgical instrument retainer 100 can also reduce the risk of patient infection by reducing the risk of surgical instrument withdrawal and replacement due to instrument breakage caused by high friction.

NOTES AND EXAMPLES

The following, non-limiting examples, detail certain aspects of the present subject matter to solve the challenges and provide the benefits discussed herein, among others.

Example 1 is a surgical instrument retainer receivable in an end effector coupler of a surgical arm, the instrument retainer comprising: a proximal component comprising: a head engageable with the end effector coupler to position the instrument retainer within the end effector coupler; a first body extending distally from the head along a longitudinal axis, the head together with the first body defining a first instrument bore extending through the head and the first body; and a proximal plurality of projections extending radially inward from the head into the first instrument bore to engage an instrument when the instrument is positioned within the first instrument bore; and a distal component defining a second instrument bore extending therethrough, and defining a body bore configured to receive the first body therein to secure the proximal component to the distal component and to align the first instrument bore with the second instrument bore, the distal component comprising: a distal plurality of projections extending radially inward from the distal component into the second instrument bore to engage the instrument when the instrument is positioned within the second instrument bore and to, together with the proximal plurality of projections, center the instrument within the first instrument bore and the second instrument bore.

In Example 2, the subject matter of Example 1 optionally includes wherein the head extends outward beyond an outer surface of the first body and is configured to contact the end effector coupler to limit distal translation of the instrument retainer within the end effector coupler.

In Example 3, the subject matter of any one or more of Examples 1-2 optionally include wherein the first body and the distal component are cylindrically shaped.

In Example 4, the subject matter of any one or more of Examples 1-3 optionally include wherein the proximal plurality of projections and the distal plurality of projections include concave contacting surfaces configured to engage with a corresponding convex exterior surface of a cylindrically shaped surgical tool.

In Example 5, the subject matter of Example 4 optionally includes wherein the proximal plurality of projections and the distal plurality of projections each include three projections.

In Example 6, the subject matter of Example 5 optionally includes wherein a radial surface of each projection is spaced from the radial surface of each adjacent projection by about 60 degrees.

In Example 7, the subject matter of any one or more of Examples 1-6 optionally include wherein a radial surface of each projection is spaced from the radial surface of each adjacent projection by about 60 degrees.

In Example 8, the subject matter of any one or more of Examples 1-7 optionally include wherein the first body further comprises a first series of coupling threads formed on an outer surface of the first body, and wherein the distal component comprises a second series of coupling threads formed in the body bore, the second series of coupling threads configured to engage the first series of coupling threads to couple the first body to the distal component.

In Example 9, the subject matter of any one or more of Examples 1-8 optionally include a beveled edge formed in a distal portion of the first body, and a chamfer formed in the distal component adjacent the body bore, the chamfer configured to be complementary to the beveled edge of the first body to position the first body within the body bore of the distal component.

Example 10 is a surgical instrument retainer receivable in an end effector coupler of a surgical arm, the instrument retainer comprising: a proximal component comprising: a head engageable with the end effector coupler to position the instrument retainer within the end effector coupler; a first body extending distally from the head along a longitudinal axis, the head together with the first body defining a first instrument bore extending through the head and the first body; and a proximal plurality of projections extending radially inward from the head into the first instrument bore to engage an instrument when the instrument is positioned within the first instrument bore; and a first series of coupling threads formed on an outer surface of the first body; and a distal component comprising: a second instrument bore extending through the distal component, the second instrument bore having a diameter equal to the first instrument bore, and defining a body bore configured to receive the first body therein to secure the proximal component to the distal component and to align the first instrument bore with the second instrument bore; and a distal plurality of projections extending radially inward from the distal component into the second instrument bore to engage the instrument when the instrument is positioned within the instrument bore and to, together with the proximal plurality of projections, center the instrument within the first instrument bore and the second instrument bore to control a trajectory of the instrument through the first instrument bore and the second instrument bore and relative to the end effector coupler; and a second series of coupling threads formed in the body bore of the distal component, the second series of coupling threads configured to engage the first series of coupling threads to couple the distal component to the proximal component.

In Example 11, the subject matter of Example 10 optionally includes wherein the head extends outward beyond an outer surface of the first body and is configured to contact the end effector coupler to limit distal translation of the instrument retainer within the end effector coupler.

In Example 12, the subject matter of any one or more of Examples 10-11 optionally include wherein the first body and the distal component are cylindrically shaped.

In Example 13, the subject matter of any one or more of Examples 10-12 optionally include wherein the proximal plurality of projections and the distal plurality of projections include concave contacting surfaces configured to engage with a corresponding convex exterior surface of a cylindrically shaped surgical tool.

In Example 14, the subject matter of any one or more of Examples 10-13 optionally include wherein a radial surface of each projection is spaced from the radial surface of each adjacent projection by about 60 degrees.

In Example 15, the subject matter of any one or more of Examples 10-14 optionally include wherein a radial surface of each projection is spaced from the radial surface of each adjacent projection by about 60 degrees.

In Example 16, the subject matter of any one or more of Examples 10-15 optionally include a beveled edge formed in a distal portion of the first body, and a chamfer formed in the body bore of the distal component, the chamfer configured to be complementary to the beveled edge of the first body to position the first body within the body bore of the distal component.

In Example 17, the subject matter of any one or more of Examples 10-16 optionally include wherein the proximal plurality of projections and the distal plurality of projections each include beveled edges at a proximal portion of each projection, the beveled edges configured to aid in positioning the surgical instrument between the proximal plurality of projections and the distal plurality of projections.

In Example 18, the subject matter of any one or more of Examples 10-17 optionally include wherein the proximal plurality of projections and the distal plurality of projections are configured to maintain a gap between the instrument and the first instrument bore to allow fluids or solids to collect within the body to limit friction between the instrument and the first and distal plurality of projections.

Example 19 is a surgical instrument retainer receivable in an end effector coupler of a surgical arm, the instrument retainer comprising: a proximal component comprising: a head engageable with the end effector coupler to position the instrument retainer within the end effector coupler; a first cylindrical body extending distally from the head along a longitudinal axis, the head together with the first cylindrical body defining a first instrument bore extending through the head and the first body; and a proximal plurality of projections extending radially inward from the head into the first instrument bore to engage an instrument when the instrument is positioned within the first instrument bore, and configured to maintain a gap between the instrument and the first instrument bore to allow blood or other particulates to collect without increasing friction between the instrument and the proximal plurality of projections; and a cylindrical distal component comprising: a second instrument bore extending through the cylindrical distal component, and defining a body bore configured to receive the first cylindrical body therein to secure the proximal component to the cylindrical distal component and to align the first instrument bore with the second instrument bore; and a distal plurality of projections extending radially inward from the cylindrical distal component into the second instrument bore to engage the instrument when the instrument is positioned within the instrument bore, and configured maintain a gap between the instrument and the second instrument bore to allow blood or other particulates to collect without increasing friction between the instrument and the distal plurality of projections; the distal plurality of projections further configured to, together with the proximal plurality of projections, align the instrument along a central axis defined by the first instrument bore and the second instrument bore.

In Example 20, the subject matter of Example 19 optionally includes wherein the proximal plurality of projections and the distal plurality of projections each include beveled edges at a proximal portion of each projection, the beveled edges configured to aid in positioning the surgical instrument along the central axis between the proximal plurality of projections and the distal plurality of projections.

In Example 21, the apparatuses, systems, or method of any one or any combination of Examples 1-20 can optionally be configured such that all elements or options recited are available to use or select from.

What is claimed is:

1. A surgical instrument retainer receivable in an end effector coupler of a surgical arm, the instrument retainer comprising:
   a proximal component comprising:
      a head engageable with the end effector coupler to position the instrument retainer within the end effector coupler;
      a first body extending distally from the head along a longitudinal axis, the head together with the first body defining a first instrument bore extending through the head and the first body; and
      a proximal plurality of projections extending radially inward from the head into the first instrument bore to engage an instrument when the instrument is positioned within the first instrument bore; and
   a distal component defining a second instrument bore extending therethrough, and defining a body bore configured to receive the first body therein to secure the proximal component to the distal component and to align the first instrument bore with the second instrument bore, the distal component comprising:
      a distal plurality of projections extending radially inward from the distal component into the second instrument bore to engage the instrument when the instrument is positioned within the second instrument bore and to, together with the proximal plurality of projections, center the instrument within the first instrument bore and the second instrument bore.

2. The instrument retainer of claim 1, wherein the head extends outward beyond an outer surface of the first body and is configured to contact the end effector coupler to limit distal translation of the instrument retainer within the end effector coupler.

3. The instrument retainer of claim 1, wherein the first body and the distal component are cylindrically shaped.

4. The instrument retainer of claim 1, wherein the proximal plurality of projections and the distal plurality of projections include concave contacting surfaces configured to engage with a corresponding convex exterior surface of a cylindrically shaped surgical tool.

5. The instrument retainer of claim 4, wherein the proximal plurality of projections and the distal plurality of projections each include three projections.

6. The instrument retainer of claim 5, wherein a radial surface of each projection is spaced from the radial surface of each adjacent projection by about 60 degrees.

7. The instrument retainer of claim 1, wherein the proximal plurality of projections and the distal plurality of projections each include four projections, wherein a radial surface of each projection is spaced from the radial surface of each adjacent projection by about 45 degrees.

8. The instrument retainer of claim 1, wherein the first body further comprises a first series of coupling threads formed on an outer surface of the first body, and wherein the distal component comprises a second series of coupling threads formed in the body bore, the second series of coupling threads configured to engage the first series of coupling threads to couple the first body to the distal component.

9. The instrument retainer of claim 1, further comprising a beveled edge formed in a distal portion of the first body, and a chamfer formed in the distal component adjacent the body bore, the chamfer configured to be complementary to the beveled edge of the first body to position the first body within the body bore of the distal component.

10. A surgical instrument retainer receivable in an end effector coupler of a surgical arm, the instrument retainer comprising:
   a proximal component comprising:
      a head engageable with the end effector coupler to position the instrument retainer within the end effector coupler;
      a first body extending distally from the head along a longitudinal axis, the head together with the first body defining a first instrument bore extending through the head and the first body; and
      a proximal plurality of projections extending radially inward from the head into the first instrument bore to engage an instrument when the instrument is positioned within the first instrument bore; and
      a first series of coupling threads formed on an outer surface of the first body; and
   a distal component comprising:
      a second instrument bore extending through the distal component, the second instrument bore having a diameter equal to the first instrument bore, and defining a body bore configured to receive the first body therein to secure the proximal component to the distal component and to align the first instrument bore with the second instrument bore; and
      a distal plurality of projections extending radially inward from the distal component into the second instrument bore to engage the instrument when the instrument is positioned within the instrument bore and to, together with the proximal plurality of projections, center the instrument within the first instrument bore and the second instrument bore to control a trajectory of the instrument through the first instrument bore and the second instrument bore and relative to the end effector coupler; and
      a second series of coupling threads formed in the body bore of the distal component, the second series of coupling threads configured to engage the first series of coupling threads to couple the distal component to the proximal component.

11. The instrument retainer of claim 10, wherein the head extends outward beyond an outer surface of the first body and is configured to contact the end effector coupler to limit distal translation of the instrument retainer within the end effector coupler.

12. The instrument retainer of claim 10, wherein the first body and the distal component are cylindrically shaped.

13. The instrument retainer of claim 10, wherein the proximal plurality of projections and the distal plurality of projections include concave contacting surfaces configured to engage with a corresponding convex exterior surface of a cylindrically shaped surgical tool.

14. The instrument retainer of claim 10, wherein the proximal plurality of projections and the distal plurality of projections each include three projections, wherein a radial surface of each projection is spaced from the radial surface of each adjacent projection by about 60 degrees.

15. The instrument retainer of claim 10, wherein the proximal plurality and the distal plurality of projections each include four projections, wherein a radial surface of each projection is spaced from the radial surface of each adjacent projection by about 45 degrees.

16. The instrument retainer of claim 10, further comprising a beveled edge formed in a distal portion of the first body, and a chamfer formed in the body bore of the distal component, the chamfer configured to be complementary to the beveled edge of the first body to position the first body within the body bore of the distal component.

17. The instrument retainer of claim 10, wherein the proximal plurality of projections and the distal plurality of projections each include beveled edges at a proximal portion of each projection, the beveled edges configured to aid in positioning the surgical instrument between the proximal plurality of projections and the distal plurality of projections.

18. The instrument retainer of claim 10, wherein the proximal plurality of projections and the distal plurality of projections are configured to maintain a gap between the instrument and the first instrument bore to allow fluids or solids to collect to limit friction between the instrument and the proximal and distal plurality of projections.

19. A surgical instrument retainer receivable in an end effector coupler of a surgical arm, the instrument retainer comprising:
  a proximal component comprising:
    a head engageable with the end effector coupler to position the instrument retainer within the end effector coupler;
    a first cylindrical body extending distally from the head along a longitudinal axis, the head together with the first cylindrical body defining a first instrument bore extending through the head and the first body; and
    a proximal plurality of projections extending radially inward from the head into the first instrument bore to engage an instrument when the instrument is positioned within the first instrument bore, and configured to maintain a gap between the instrument and the first instrument bore to allow blood or other particulates to collect without increasing friction between the instrument and the proximal plurality of projections; and
  a cylindrical distal component comprising:
    a second instrument bore extending through the cylindrical distal component, and defining a body bore configured to receive the first cylindrical body therein to secure the proximal component to the cylindrical distal component and to align the first instrument bore with the second instrument bore; and
    a distal plurality of projections extending radially inward from the cylindrical distal component into the second instrument bore to engage the instrument when the instrument is positioned within the instrument bore, and configured maintain a gap between the instrument and the second instrument bore to allow blood or other particulates to collect without increasing friction between the instrument and the distal plurality of projections;
    the distal plurality of projections further configured to, together with the proximal plurality of projections, align the instrument along a central axis defined by the first instrument bore and the second instrument bore.

20. The instrument retainer of claim 19, wherein the proximal plurality of projections and the distal plurality of projections each include beveled edges at a proximal portion of each projection, the beveled edges configured to aid in positioning the surgical instrument along the central axis between the proximal plurality of projections and the distal plurality of projections.

* * * * *